United States Patent [19]
Daniel et al.

[11] Patent Number: 6,053,932
[45] Date of Patent: *Apr. 25, 2000

[54] DISTAL PROTECTION DEVICE

[75] Inventors: John M. K. Daniel, Hopkins; Robert L. Cassell, Otsego; David J. Holtan, Rogers, all of Minn.

[73] Assignee: SciMed Life Systems, Inc., Maple Grove, Minn.

[ * ] Notice: This patent is subject to a terminal disclaimer.

[21] Appl. No.: 09/082,096

[22] Filed: May 20, 1998

Related U.S. Application Data

[63] Continuation of application No. 08/810,825, Mar. 6, 1997, Pat. No. 5,814,064.

[51] Int. Cl.$^7$ .................................................. A61M 29/00
[52] U.S. Cl. ........................ 606/200; 606/159; 606/198; 604/104
[58] Field of Search ...................... 606/1, 159; 604/96, 604/101, 104–108

[56] References Cited

U.S. PATENT DOCUMENTS

| | | |
|---|---|---|
| 4,425,908 | 1/1984 | Simon . |
| 4,447,227 | 5/1984 | Kotsanis . |
| 4,590,938 | 5/1986 | Segura et al. . |
| 4,706,671 | 11/1987 | Weinrib . |
| 4,723,549 | 2/1988 | Wholey et al. . |
| 4,728,319 | 3/1988 | Masch . |
| 4,790,812 | 12/1988 | Hawkins, Jr. et al. . |
| 4,790,813 | 12/1988 | Kensey . |

(List continued on next page.)

FOREIGN PATENT DOCUMENTS

| | | |
|---|---|---|
| 0 737 450 A1 | 10/1996 | European Pat. Off. . |
| 2821048 | 8/1979 | Germany . |
| 764684 | 9/1980 | U.S.S.R. . |
| 2 020 557 | 1/1983 | United Kingdom . |
| Wo 94/24946 | 11/1994 | WIPO . |
| WO 96/01591 | 1/1996 | WIPO . |
| WO 98/33443 | 8/1998 | WIPO . |

OTHER PUBLICATIONS

"A New Percutaneous Vena Cava Filter", by Andrew Cragg et al., *AJR*, 141, Sep. 1983, pp. 601–604.

"Nonsurgical Placement of Arterial Endoprosthesis: A New Technique Using Nitinol Wire", by Andrew Cragg et al., *AJR*, Apr. 1983, pp. 261–263.

"Long–term Patency of the Ductus Arteriosus After Ballon Dilatation: An Experimental Study", by Gunnar Lund, M.D., et al., *AJR*, Sep. 1983;, p. 772.

*The Journal of Invasive Cardiology*, vol. 8, Supplement E, 1996, "Stents Don't Require Systemic Anticoagulation . . . But the Technique (and Results) Must Be Optimal", by Issaam Moussa, MD, et al., pp. 3E–30E, Health Management Publications, Inc.

*Primary Examiner*—Gary Jackson
*Assistant Examiner*—William W. Lewis
*Attorney, Agent, or Firm*—Crompton, Seager & Tufte, LLC

[57] ABSTRACT

An emboli capturing system captures emboli in blood flowing in the vasculature. The emboli capturing system includes a guidewire having a longitudinal axis and defining a lumen along at least a portion thereof. An expandable member is coupled to a distal portion of the guidewire and has an interior being in fluid communication with the lumen in the guidewire. The expandable member is configured to receive fluid through the lumen to expand radially outwardly relative to the guidewire and have fluid removed from the interior thereof to collapse radially inwardly relative to the guidewire. The expandable member, when expanded, has a spaced portion thereof spaced radially outwardly from the guidewire. An emboli capturing device is coupled to the expandable member and is configured to deploy radially outwardly relative to the guidewire upon expansion of the expandable member.

10 Claims, 9 Drawing Sheets

U.S. PATENT DOCUMENTS

| | | |
|---|---|---|
| 4,794,928 | 1/1989 | Kletschka . |
| 4,873,978 | 10/1989 | Ginsburg . |
| 4,926,858 | 5/1990 | Gifford, III et al. . |
| 4,998,539 | 3/1991 | Delsanti . |
| 5,011,488 | 4/1991 | Ginsburg . |
| 5,053,008 | 10/1991 | Bajaj . |
| 5,071,407 | 12/1991 | Termin et al. . |
| 5,100,423 | 3/1992 | Fearnot . |
| 5,102,415 | 4/1992 | Guenther et al. . |
| 5,108,419 | 4/1992 | Reger et al. . |
| 5,190,546 | 3/1993 | Jervis . |
| 5,329,942 | 7/1994 | Gunther et al. . |
| 5,354,310 | 10/1994 | Garnic et al. . |
| 5,376,100 | 12/1994 | Lefebvre . |
| 5,421,832 | 6/1995 | Lefebvre . |
| 5,549,626 | 8/1996 | Miller et al. . |
| 5,695,519 | 12/1997 | Summers et al. . |
| 5,814,064 | 9/1998 | Daniel et al. . |

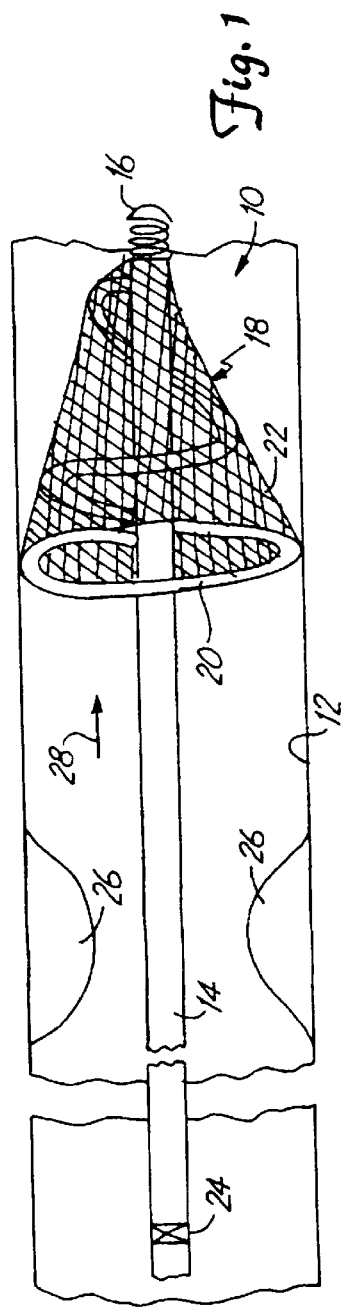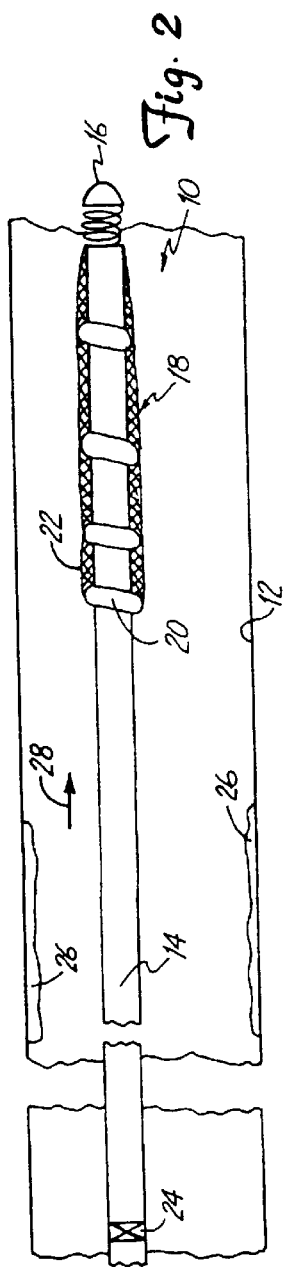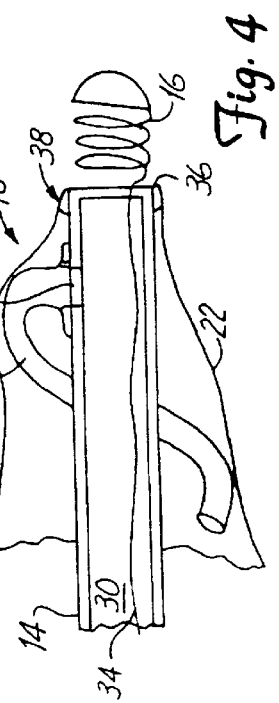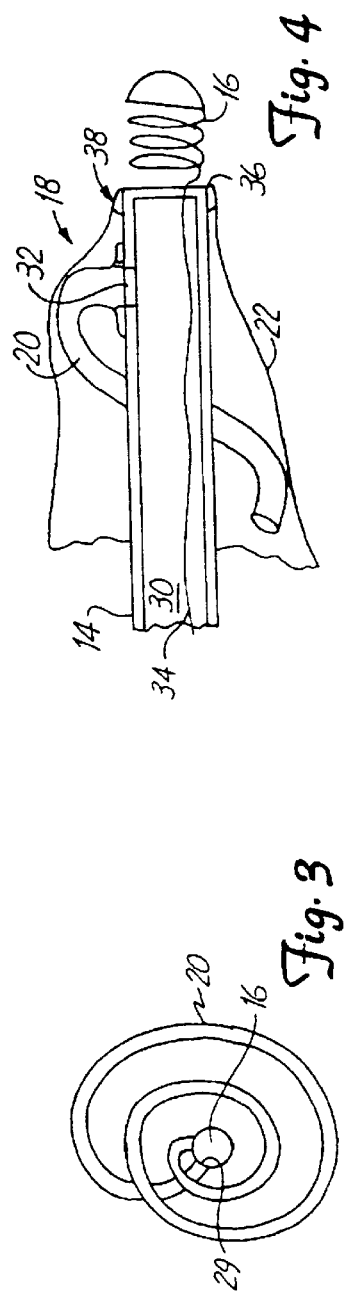

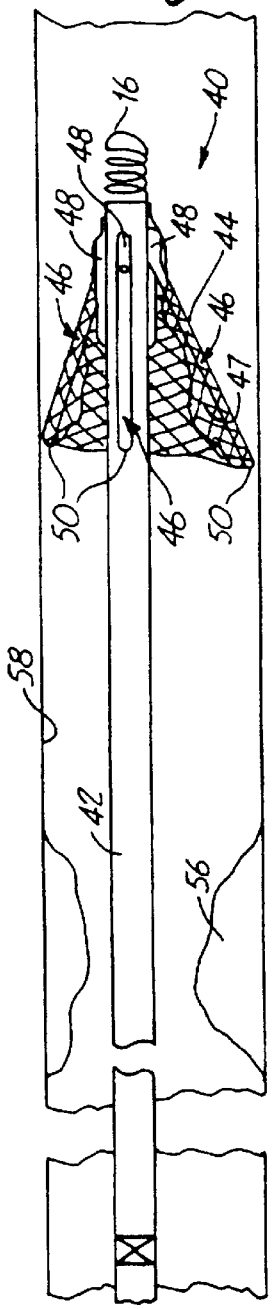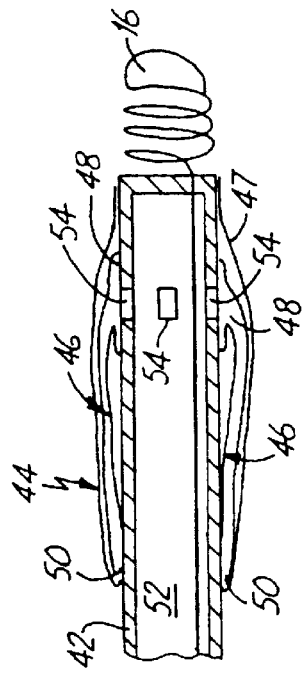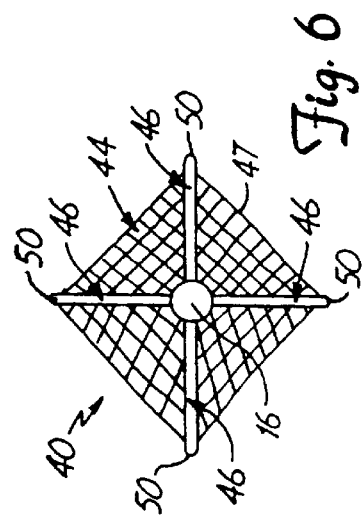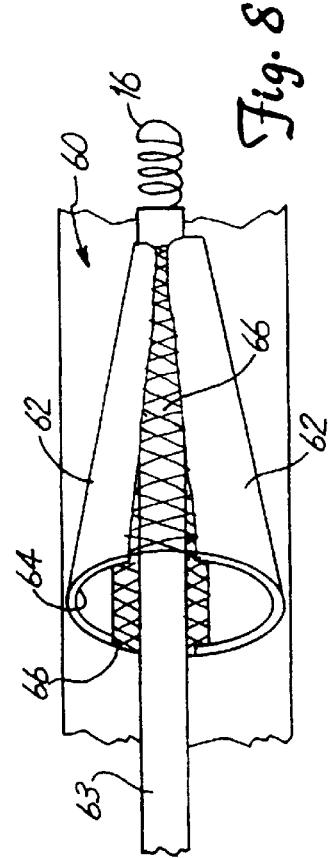

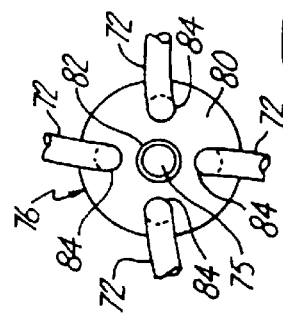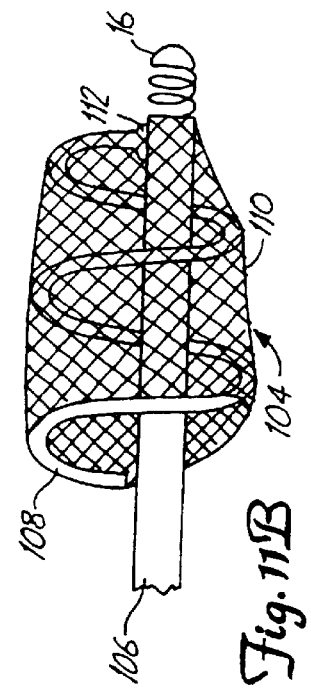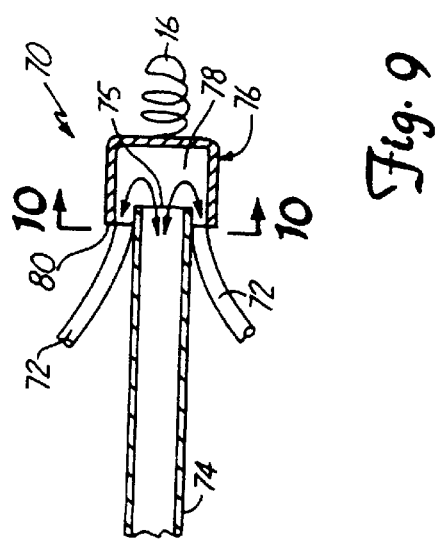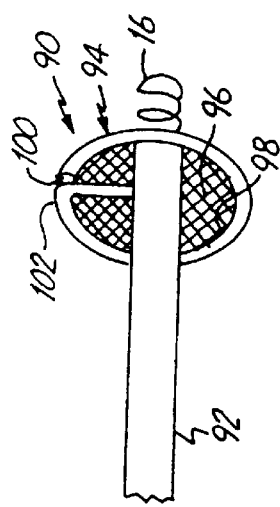

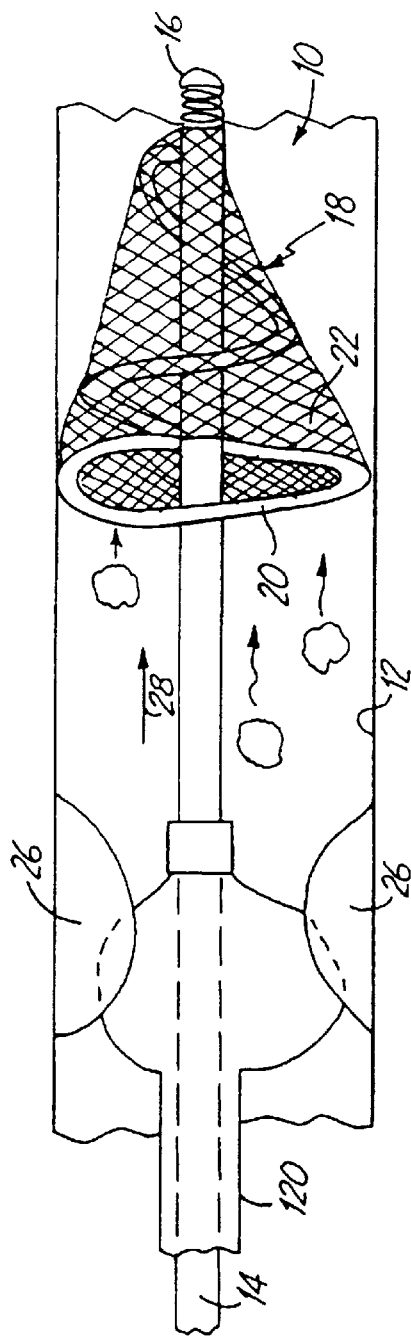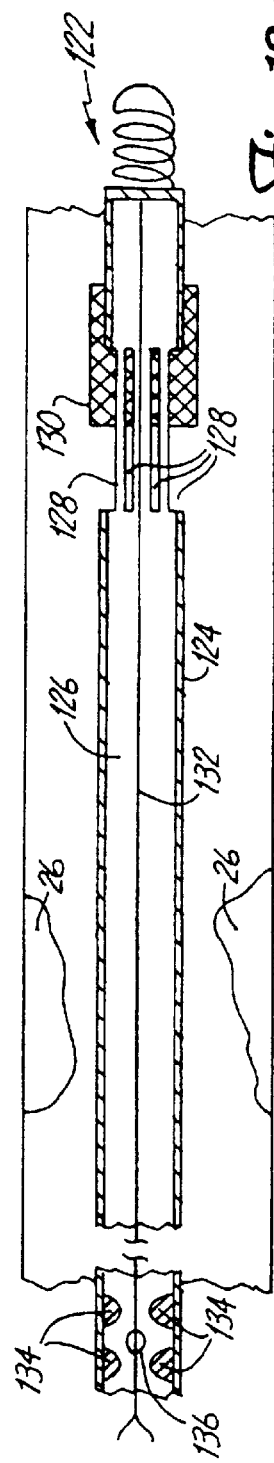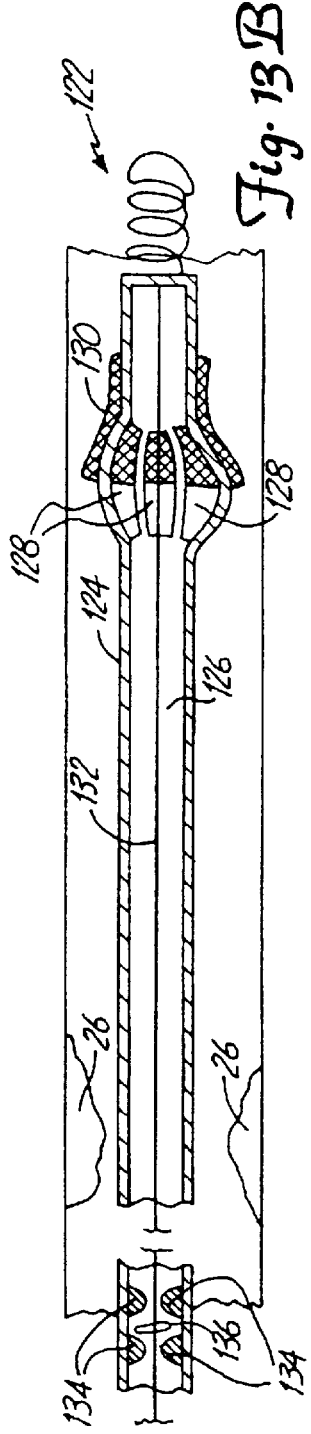

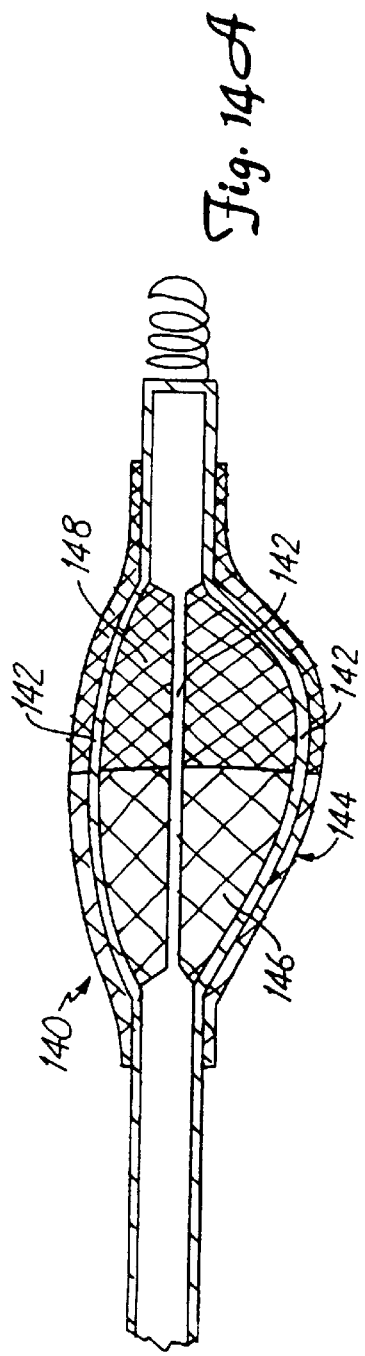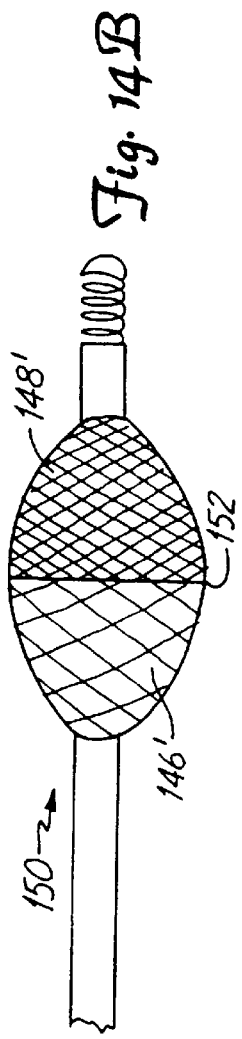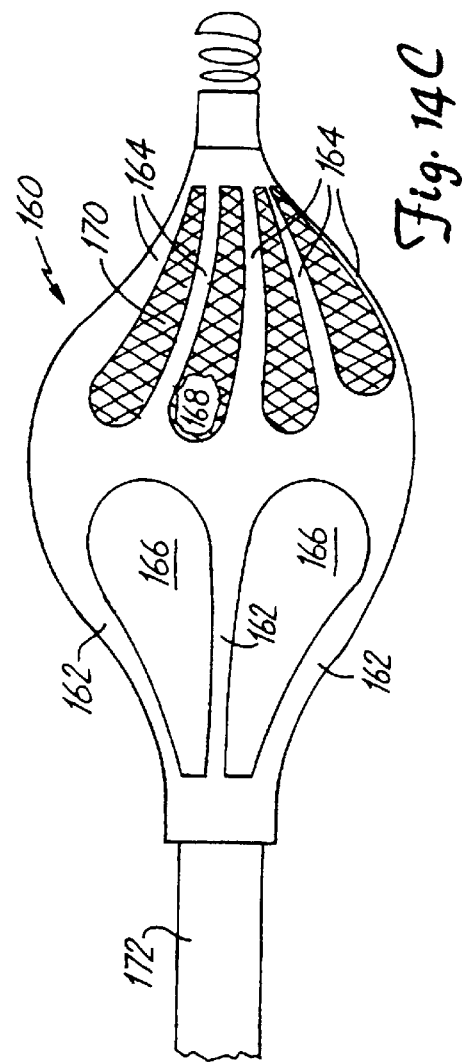

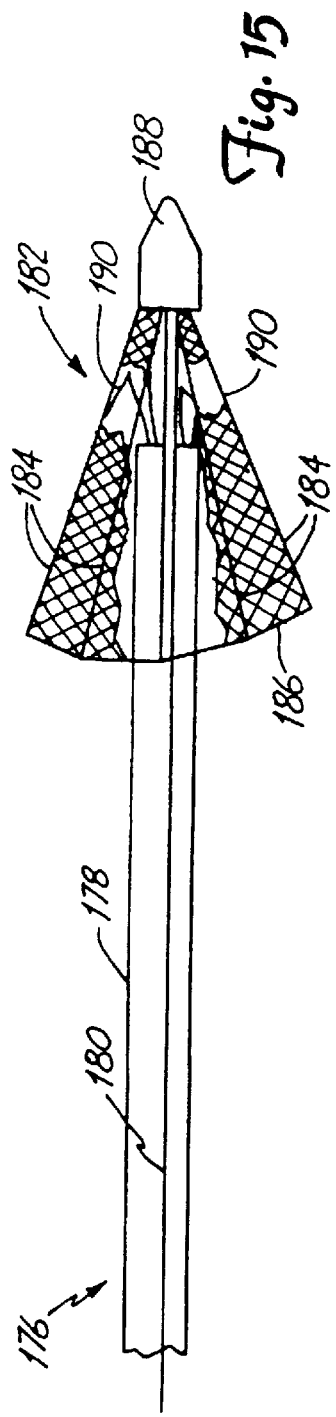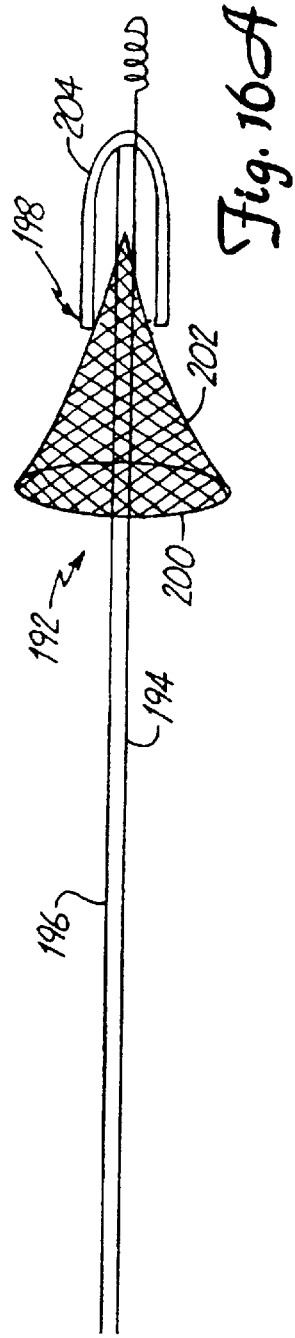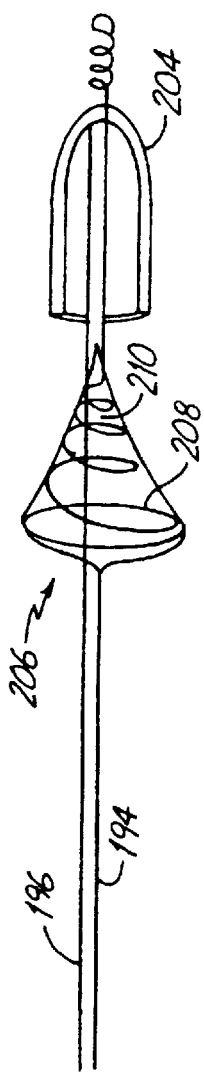

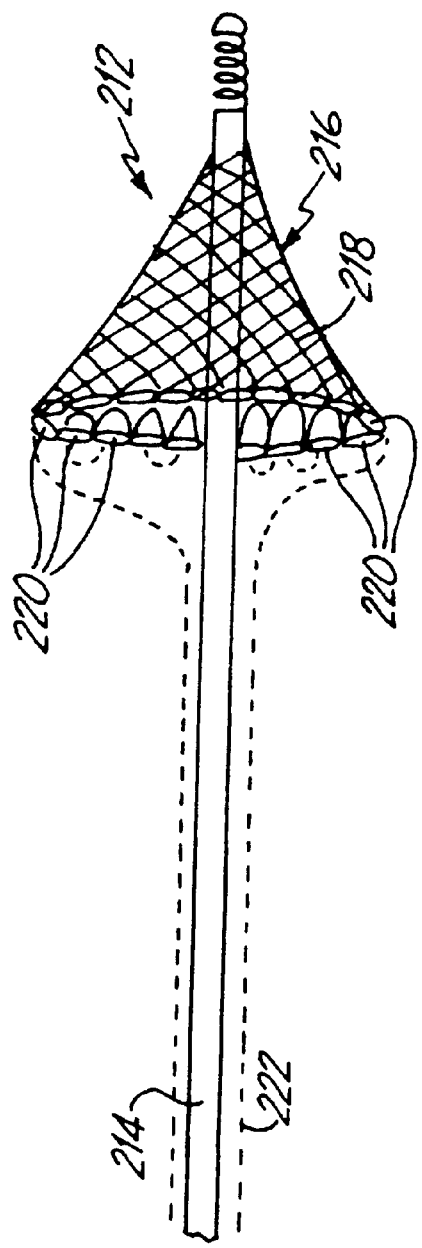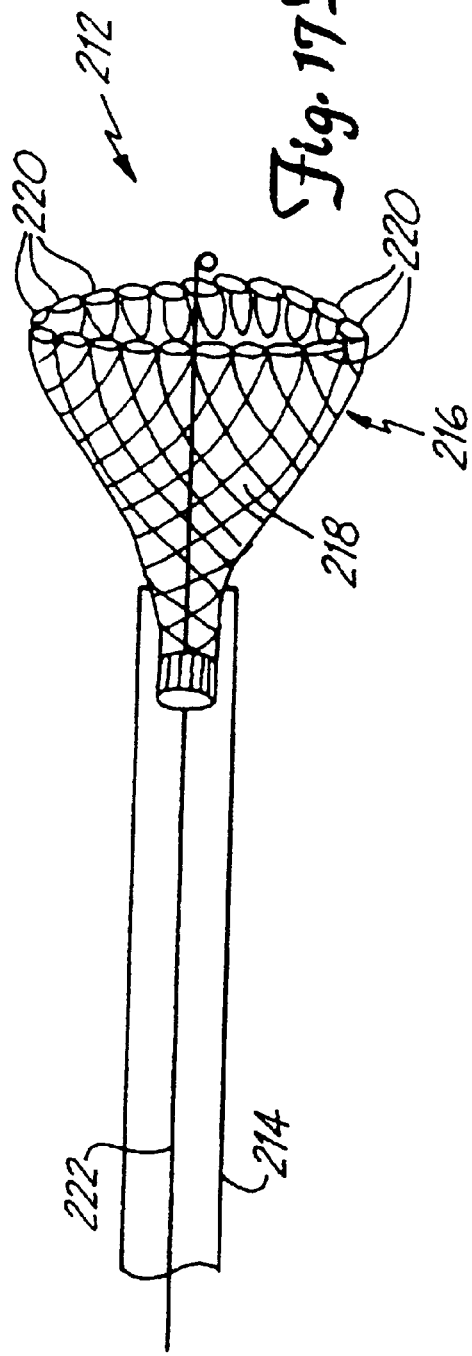

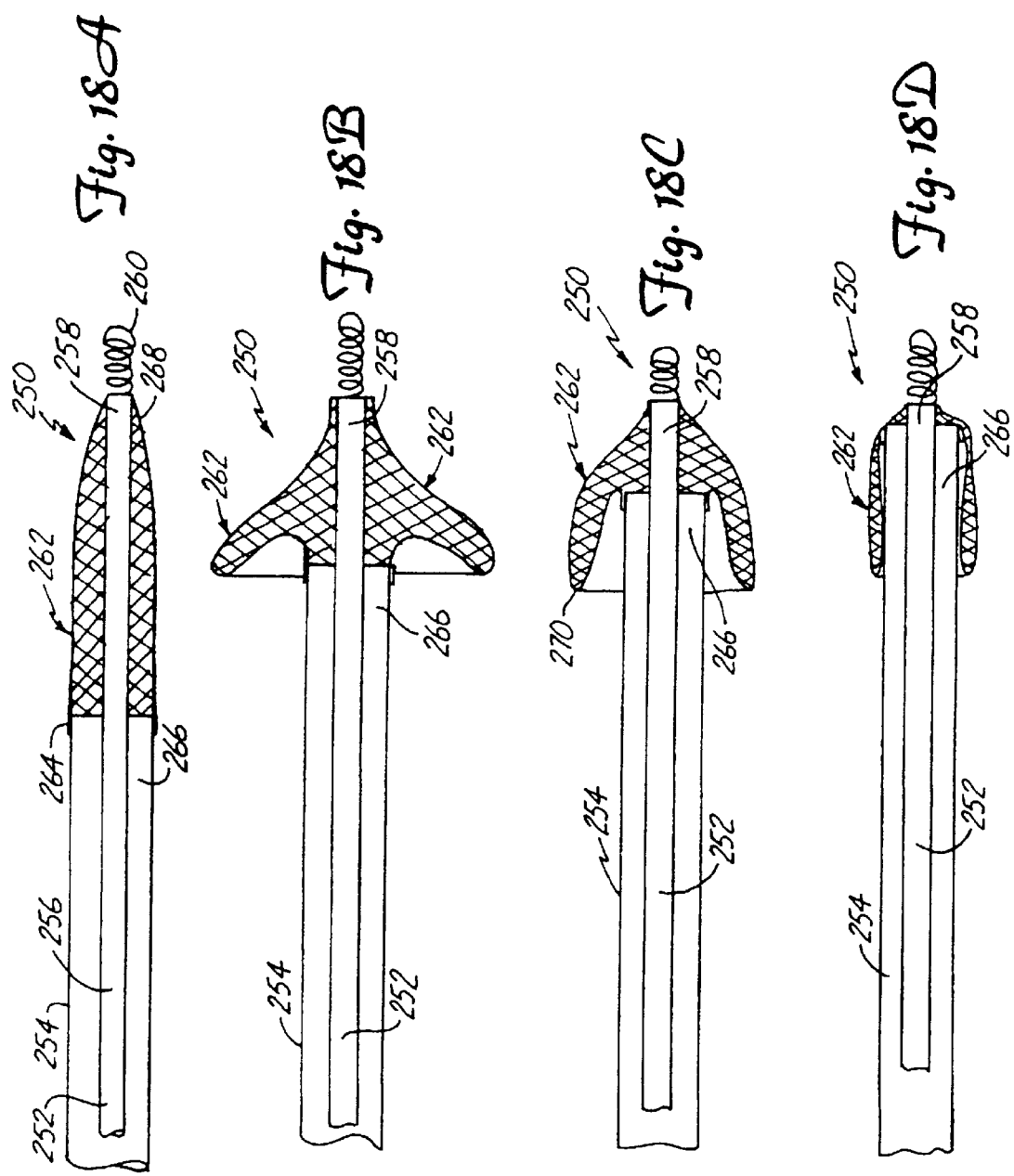

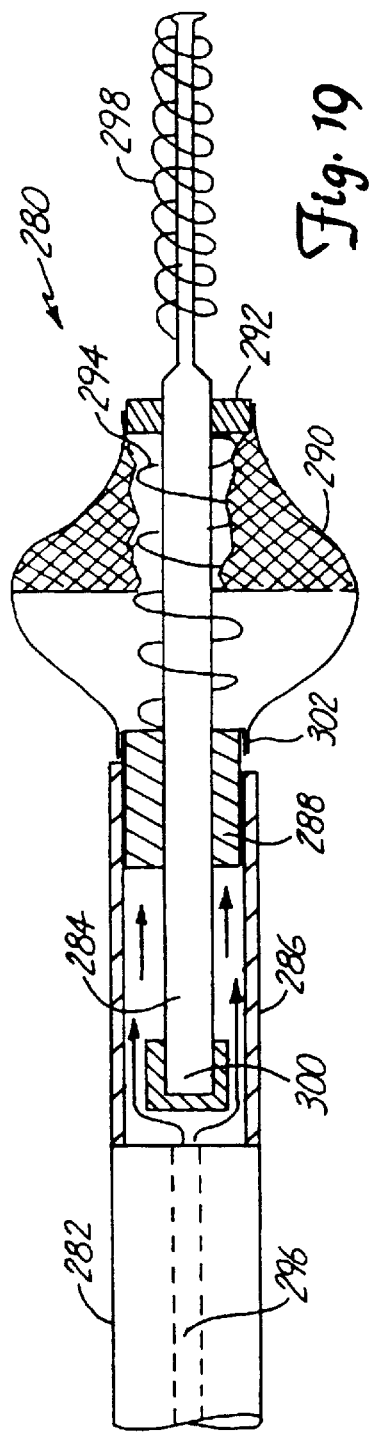
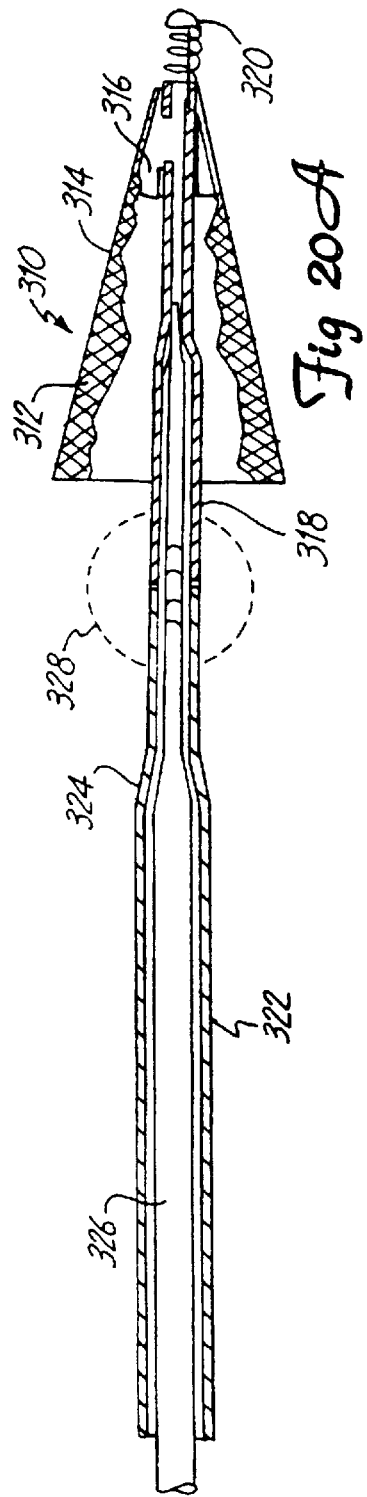
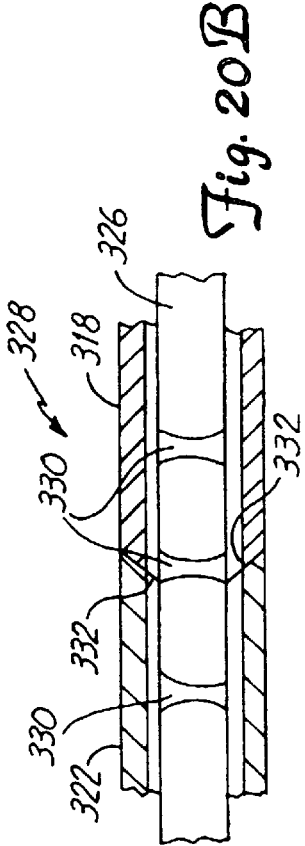

DISTAL PROTECTION DEVICE

INCORPORATION BY REFERENCE

The present application claims priority from, and is a continuation of, U.S. patent application Ser. No. 08/810,825 filed on Mar. 6, 1997, now U.S. Pat. No. 5,814,064 entitled "DISTAL PROTECTION DEVICE", and assigned to the same assignee as the present application.

The following patent application is hereby incorporated by reference U.S. patent application Ser. No. 08/810,825, now U.S. Pat. No. 5,814,064 entitled "DISTAL PROTECTION DEVICE," which was filed on even date herewith and assigned to the same assignee as the present application.

BACKGROUND OF THE INVENTION

The present invention deals with an emboli capturing system. More specifically, the present invention deals with an emboli capturing system for capturing embolic material in a blood vessel during an atherectomy or thrombectomy procedure.

Blood vessels can become occluded (blocked) or stenotic (narrowed) in one of a number of ways. For instance, a stenosis may be formed by an atheroma which is typically a harder, calcified substance which forms on the lumen walls of the blood vessel. Also, the stenosis can be formed of a thrombus material which is typically much softer than an atheroma, but can nonetheless cause restricted blood flow in the lumen of the blood vessel. Thrombus formation can be particularly problematic in a saphenous vein graft (SVG).

Two different procedures have developed to treat a stenotic lesion (stenosis) in vasculature. The first is to deform the stenosis to reduce the restriction within the lumen of the blood vessel. This type of deformation (or dilatation) is typically performed using balloon angioplasty.

Another method of treating stenotic vasculature is to attempt to completely remove either the entire stenosis, or enough of the stenosis to relieve the restriction in the blood vessel. Removal of the stenotic lesion has been done through the use of radio frequency (RF) signals transmitted via conductors, and through the use of lasers, both of which treatments are meant to ablate (i.e., super heat and vaporize) the stenosis. Removal of the stenosis has also been accomplished using thrombectomy or atherectomy. During thrombectomy and atherectomy, the stenosis is mechanically cut or abraded away from the vessel.

Certain problems are encountered during thrombectomy and atherectomy. The stenotic debris which is separated from the stenosis is free to flow within the lumen of the vessel. If the debris flows distally, it can occlude distal vasculature and cause significant problems. If it flows proximally, it can enter the circulatory system and form a clot in the neural vasculature, or in the lungs, both of which are highly undesirable.

Prior attempts to deal with the debris or fragments have included cutting the debris into such small pieces (having a size on the order of a blood cell) that they will not occlude vessels within the vasculature. However, this technique has certain problems. For instance, it is difficult to control the size of the fragments of the stenotic lesion which are severed. Therefore, larger fragments can be severed accidentally. Also, since thrombus is much softer than an atheroma, it tends to break up easier when mechanically engaged by a cutting instrument. Therefore, at the moment that the thrombus is mechanically engaged, there is a danger that it can be dislodged in large fragments which would occlude the vasculature.

Another attempt to deal with debris severed from a stenosis is to remove the debris, as it is severed, using suction. However, it may be necessary to pull quite a high vacuum in order to remove all of the pieces severed from the stenosis. If a high enough vacuum is not used, all of the severed pieces will not be removed. Further, when a high vacuum is used, this can tend to cause the vasculature to collapse.

A final technique for dealing with the fragments of the stenosis which are severed during atherectomy is to place a device distal to the stenosis during atherectomy to catch the pieces of the stenosis as they are severed, and to remove those pieces along with the capturing device when the atherectomy procedure is complete. Such capture devices have included expandable filters which are placed distal of the stenosis to capture stenosis fragments. However, such prior devices have typically been supported by over-the-wire devices such as balloon angioplasty catheters. Over-the-wire devices of this type have a fairly large outer diameter which can, under some circumstances, be undesirable.

SUMMARY OF THE INVENTION

An emboli capturing system captures emboli in blood flowing in the vasculature. The emboli capturing system includes a guidewire having a longitudinal axis and defining a lumen along at least a portion thereof. An expandable member is coupled to a distal portion of the guidewire and has an interior being in fluid communication with the lumen in the guidewire. The expandable member is configured to receive fluid through the lumen to expand radially outwardly relative to the guidewire and have fluid removed from the interior thereof to collapse radially inwardly relative to the guidewire. The expandable member, when expanded, has a spaced portion thereof spaced radially outwardly from the guidewire. An emboli capturing device is coupled to the expandable member and is configured to deploy radially outwardly relative to the guidewire upon expansion of the expandable member.

BRIEF DESCRIPTION OF THE DRAWINGS

FIG. 1 shows a distal protection device of the present invention in a deployed position.

FIG. 2 shows the distal protection device shown in FIG. 1 in a collapsed position.

FIG. 3 shows an end view of a portion of the distal protection device shown in FIGS. 1 and 2.

FIG. 4 shows a cross-sectional view of a portion of the distal protection device shown in FIGS. 1–3 in the deployed position.

FIG. 5 shows a second embodiment of the distal protection device according to the present invention in a deployed position.

FIG. 6 shows an end view of the distal protection device shown in FIG. 5.

FIG. 7 shows a cross-sectional view of the distal protection device shown in FIGS. 5 and 6 in the collapsed position.

FIG. 8 shows a third embodiment of a distal protection device according to the present invention in a deployed position.

FIG. 9 is a side sectional view of an alternate embodiment illustrating how the expandable members of the present invention are attached to a guidewire.

FIG. 10 is a sectional view taken along section lines 10—10 in FIG. 9.

FIGS. 11A and 11B show a fourth and fifth embodiment, respectively, of a distal protection device according to the present invention in a deployed position.

FIG. 12 illustrates the operation of a distal protection device in accordance with the present invention.

FIGS. 13A–17B show additional embodiments of distal protection devices which expand and collapse based on movement of a mechanical actuator.

FIGS. 18A–18D illustrate an additional embodiment of a distal protection device which is deployed and collapsed using a rolling flap configuration.

FIG. 19 illustrates another embodiment in accordance with the present invention in which the protection device is deployed using fluid pressure and a movable collar.

FIGS. 20A and 20B illustrate another aspect of the present invention in which two longitudinally movable members used to deploy the distal protection device are disconnectably locked to one another.

DETAILED DESCRIPTION OF THE PREFERRED EMBODIMENTS

FIG. 1 illustrates protection device 10 in a deployed position within the lumen of a blood vessel 12. Protection device 10 preferably includes hollow guidewire 14 (or a hypotube having the same general dimensions as a guidewire) having a coil tip 16, and a capturing assembly 18. Capturing assembly 18, in the embodiment shown in FIG. 1, includes an inflatable and expandable member 20 and mesh 22.

An interior of expandable member 20 is preferably coupled for fluid communication with an inner lumen of guidewire 14 at a distal region of guidewire 14. When deployed, inflatable member 20 inflates and expands to the position shown in FIG. 1 such that capturing assembly 18 has an outer periphery which approximates the inner periphery of lumen 12.

Mesh 22 is preferably formed of woven or braided fibers or wires, or a microporous membrane, or other suitable filtering or netting-type material. In one preferred embodiment, mesh 22 is a microporous membrane having holes therein with a diameter of approximately 100 $\mu$m. Mesh 22 can be disposed relative to inflatable member 20 in a number of different ways. For example, mesh 22 can be formed of a single generally cone-shaped piece which is secured to the outer or inner periphery of inflatable member 20. Alternatively, mesh is 22 can be formed as a spiral strip which is secured about the outer or inner periphery of inflatable member 20 filling the gaps between the loops of inflatable member 20. Alternatively, mesh 22 can be formed of a number of discrete pieces which are assembled onto inflatable member 20.

Hollow guidewire 14 preferably has a valve 24 coupled in a proximal portion thereof. During operation, a syringe is preferably connected to the proximal end of guidewire 14, which preferably includes a fluid hypotube. The syringe is used to pressurize the fluid such that fluid is introduced through the lumen of hollow guidewire 14, through valve 24, and into inflatable member 20. Upon being inflated, inflatable member 20 expands radially outwardly from the outer surface of guidewire 14 and carries mesh 22 into the deployed position shown in FIG. 1. In this way, capturing assembly, or filter assembly, 18 is deployed distally of stenosis 26 so that stenosis 26 can be severed and fragmented, and so the fragments from stenosis 26 are carried by blood flow (indicated by arrow 28) into the basket or chamber formed by the deployed filter assembly 18. Filter assembly 18 is then collapsed and removed from vessel 12 with the fragments of stenosis 26 contained therein.

FIG. 2 illustrates protection device 10 with filter assembly 18 in the collapsed position. Similar items to those shown in FIG. 1 are similarly numbered. FIG. 2 illustrates that mesh 22 is easily collapsible with inflatable member 20. In order to collapse filter assembly 18, fluid is preferably removed from inflatable member 20 through the lumen of hollow guidewire 14 and through two-way valve 24. This can be done using the syringe to pull a vacuum, or using any other type of suitable fluid removal system.

Inflatable member 20 is preferably formed of a material having some shape memory. Thus, when inflatable member 20 is collapsed, it collapses to approximate the outer diameter of hollow guidewire 14. In one preferred embodiment, inflatable member 20 is formed of a resilient, shape memory material such that it is inflated by introducing fluid under pressure through the lumen in hollow guidewire 14 into inflatable member 20. When pressure is released from the lumen in hollow guidewire 14, inflatable member 20 is allowed to force fluid out from the interior thereof through twoway valve 24 and to resume its initial collapsed position. Again, this results in filter assembly 18 assuming its collapsed position illustrated in FIG. 2.

FIG. 3 illustrates a view taken from the distal end of device 10 with mesh 22 removed for clarity. FIG. 3 shows that, when inflatable member 20 is deployed outwardly, mesh 22 (when deployed between the loops of inflatable member 20) forms a substantially lumen-filling filter which allows blood to flow therethrough, but which provides a mechanism for receiving and retaining stenosis fragments carried into mesh 22 by blood flow through the vessel.

FIG. 3 also shows that inflatable member 20 preferably has a proximal end portion 29 which is connected to the outer periphery of guidewire 14. Although end 29 need not be connected to guidewire 14, it is preferably connected using adhesive or any other suitable connection mechanism. By fixedly connecting proximal end portion 29 to guidewire 14, this increases the stability of the filter assembly 18 upon deployment.

FIG. 4 is a cross-sectional view of a portion of protection device 10. FIG. 4 shows protection device 10 with filter assembly 18 in the expanded or deployed position. FIG. 4 also better illustrates that guidewire 14 is hollow and has a longitudinal lumen 30 extending therethrough. Longitudinal lumen 30 is connected in fluid communication with an interior of inflatable member 20 through aperture 32 which is provided in the wall of guidewire 14. FIG. 4 also shows that, in one preferred embodiment, a core wire 34 extends through lumen 30 from a proximal end thereof where it is preferably brazed to a portion of a hypotube which may be connected to the proximal portion of guidewire 14. The core wire 34 extends to the distal end of guidewire 14 where it is connected to coil tip 16. In one preferred embodiment, coil tip 16 is brazed or otherwise welded or suitably connected to the distal portion of core wire 34.

FIG. 4 further shows that, in the preferred embodiment, inflatable member 20 inflates to a generally helical, conical shape to form a basket opening toward the proximal end of guidewire 14. FIG. 4 further illustrates, in the preferred embodiment, mesh 22 has a distal portion 38 which is connected to the exterior surface of guidewire 14, at a distal region thereof, through adhesive 36 or any other suitable connection mechanism.

FIG. 5 illustrates a second embodiment of a distal protection device 40 in accordance with the present invention. Device 40 includes hollow guidewire 42, filter assembly 44 and coil tip 16. Filter assembly 44 includes a plurality of inflatable struts 46 and mesh 47. Each strut 46 has a distal end 48 and proximal end 50. Inflatable struts 46 also have an interior which is coupled in fluid communication, through distal end 48 thereof, with the lumen in hollow guidewire 42. Struts 46 are preferably configured such that, upon being inflated, the proximal ends 50 deploy radially outwardly away from the outer surface of hollow guidewire 42 to assume a dimension which approximates the inner dimension of lumen 58 in which they are inserted.

Mesh 47, as with mesh 22 shown in FIG. 1, is deployed either on the outer or inner surface of inflatable struts 46, such that, when the inflatable struts 46 are deployed radially outwardly, mesh 47 forms a generally conical basket opening toward the proximal end of hollow guidewire 42. As with the embodiment shown in FIG. 1, mesh 47 can be applied to either the outer or the inner surface of struts 46. It can be applied to struts 46 as one unitary conical piece which is adhered about distal ends 48 of struts 46 using adhesive (or about the distal end of guidewire 42 using adhesive) and secured to the surface of the struts 46 also using adhesive. Alternatively, mesh 47 can be applied to struts 46 in a plurality of pieces which are individually or simultaneously secured to, and extend between, struts 46.

FIG. 6 is an end view of distal protection device 40 shown in FIG. 5 taken from the distal end of distal protection device 40. When struts 46 are deployed outwardly, mesh 47 forms a substantially lumen-filling filter which allows blood to flow therethrough, but which provides a mechanism for receiving and retaining stenosis fragments from stenosis 56 carried into mesh 47 by blood flow through the vessel.

FIG. 7 is a cross-sectional view of a portion of distal protection device 40 shown in FIGS. 5 and 6. FIG. 7 shows filter assembly 44 in the collapsed position in which it approximates the outer diameter of guidewire 42. FIG. 7 also shows that, in the preferred embodiment, the distal ends 48 of struts 46 are in fluid communication with an inner lumen 52 in hollow guidewire 42 through apertures 54 in the wall of guidewire 42.

FIG. 8 illustrates another embodiment of a distal protection device 60 in accordance with the present invention. Distal protection device 60 is similar to those shown in other figures, and similar items are similarly numbered. However, distal protection device 60 includes hollow guidewire 63 which has a lumen in fluid communication with an interior of a pair of inflatable struts 62. Inflatable struts 62 have an inner surface 64 which is generally concave, or hemispherical, or otherwise appropriately shaped such that it extends about a portion of the outer surface of hollow guidewire 63. Mesh portions 66 extend between the inflatable struts 62 so that inflatable struts 62 and mesh portions 66, when deployed outwardly as shown in FIG. 8, form a basket shape which opens toward the proximal end of hollow guidewire 63.

FIG. 9 illustrates another system for attaching inflatable struts to a hollow guidewire for a distal protection device 70 in accordance with the present invention. Distal protection device 70 is similar to the distal protection devices shown in the previous figures in that a plurality of inflatable struts 72 are provided and preferably have a mesh portion extending therebetween. For the sake of clarity, the mesh portion is eliminated from FIG. 9. However it will be understood that, when deployed, distal protection device 70 forms a generally basket-shaped filter assembly which opens toward the proximal end of hollow guidewire 74.

In the embodiment shown in FIG. 9, hollow guidewire 74 has a distal end 75 which is open. An endcap 76 is disposed about the distal end 75 of hollow guidewire 74 and defines an internal chamber or passageway 78. Endcap 76 has a proximal end 80 which has openings therein for receiving the ends of inflatable struts 72. Thus, in order to inflate inflatable struts 72, the operator pressurizes fluid within the lumen of hollow guidewire 74 forcing fluid out through distal end 75 of hollow guidewire 74, through passageway 78, and into inflatable struts 72. In order to collapse distal protection device 70, the operator draws a vacuum which pulls the fluid back out of inflatable struts 72, through passageway 78 and, if necessary, into the lumen of hollow guidewire 74.

FIG. 10 is an end view of endcap 76 taken along lines 10—10 in FIG. 9. FIG. 10 shows that proximal end 80 of endcap 76 preferably includes a first generally central aperture 82 for receiving the distal end of hollow guidewire 74. Aperture 82 is sized just larger than, or approximating, the outer diameter of hollow guidewire 74 such that it fits snugly over the distal end 75 of hollow guidewire 74. Endcap 76 is then fixedly connected to the distal end 75 of hollow guidewire 74 through a friction fit, a suitable adhesive, welding, brazing, or another suitable connection technique.

FIG. 10 also shows that proximal end 80 of endcap 76 includes a plurality of apertures 84 which are spaced from one another about end 80. Apertures 84 are sized to receive open ends of inflatable struts 72. In the preferred embodiment, inflatable struts 72 are secured within apertures 84 using a suitable adhesive, or another suitable connection technique. Also, in the preferred embodiment, spring tip 16 is embedded in, or otherwise suitably connected to, endcap 76.

FIGS. 11A and 11B show two other preferred embodiments of a distal protection device in accordance with the present invention. FIG. 11A shows distal protection device 90 which includes hollow guidewire 92 having a lumen running therethrough, inflatable member 94 and mesh portion 96. FIG. 11A shows that inflatable member 94, when inflated, forms a ring about the outer surface of hollow guidewire 92. The ring has an inner periphery 98 which is spaced from the outer surface of hollow guidewire 92 substantially about the entire radial periphery of hollow guidewire 92. Mesh portion 96 extends between the outer surface of hollow guide 92 and the inner periphery 98 of inflatable member 94. Thus, a substantially disc-shaped filter assembly is provided upon deployment of distal protection device 90. As with the other embodiments, deployment of distal protection device 90 is accomplished by providing fluid through the inner lumen of hollow guidewire 92 into an interior of inflatable member 94 which is in fluid communication with the inner lumen of hollow guidewire 92.

In one preferred embodiment, end 100 of inflatable member 94 is coupled to a coupling portion 102 of inflatable member 94 such that stability is added to inflatable member 94, when it is inflated.

FIG. 11B illustrates another distal protection device 104 which includes a hollow guidewire 106 and an inflatable member 108. Device 104 is similar to distal protection device 90 except that, rather than having only a single inflatable ring upon deployment of distal protection device 104, a plurality of generally equal-diameter rings are formed into a helix shape. In the preferred embodiment, distal protection device 104 includes a mesh sleeve 110 which extends about the outer or inner surface of the helix formed by inflatable member 108. In one embodiment, mesh sleeve 110 is connected to the outer surface of hollow guidewire 106 in a region 112 proximate, but distal of, inflatable member 108. In another preferred embodiment, the proximal end of mesh sleeve 110 is connected to the outer perimeter of inflatable member 108. Thus, distal protection device 104 forms a generally basket-shaped filter assembly which opens toward a proximal end of guidewire 106.

As with the other embodiments, both distal protection device 90 shown in FIG. 11A and distal protection device 104 shown in FIG. 11B are preferably collapsible. Therefore, when collapsed, the distal protection devices 90 and 104 preferably have an outer dimension which approximates the outer dimension of hollow guidewires 92 and 106, respectively. Further, as with the other embodiments, distal protection devices 90 and 104 can either be biased in the deployed or collapsed positions, and deployment and collapse can be obtained either by pulling a vacuum, or pressurizing the fluid within the lumen of the hollow guidewires 92 and 106.

FIG. 12 illustrates the use of a distal protection device in accordance with the present invention. For the sake of clarity, the present description proceeds with respect to distal protection device 10 only. Device 10 is shown filtering stenosis fragments from the blood flowing through the lumen of vessel 12. FIG. 12 also shows a dilatation device 120 which can be any suitable dilatation device for dilating, cutting, fragmenting, or abrading, portions of stenosis 26. In the preferred embodiment, device 120 is used in an over-the-wire fashion over hollow guidewire 14. Thus, filter assembly 18 is first advanced (using guidewire 14) distal of stenosis 26. Then, filter assembly 18 is deployed outwardly to the expanded position. Dilatation device 120 is then advanced over guidewire 14 to stenosis 26 and is used to fragment or abrade stenosis 26. The fragments are received within the basket of filter assembly 18. Filter assembly 18 is then collapsed, and filter assembly 18 and dilatation device 120 are removed from vessel 12. Alternatively, dilatation device 120 can be removed first and filter assembly 18 is then removed along with guidewire 14.

It should be noted that the stenosis removal device (or atherectomy catheter) 120 used to fragment stenosis 26 can be advanced over guidewire 14. Therefore, the device according to the present invention is dual functioning in that it captures emboli and serves as a guidewire. The present invention does not require adding an additional device to the procedure. Instead, the present invention simply replaces a conventional guidewire with a multi-functional device.

FIGS. 13A–17B illustrate embodiments of various distal protection devices wherein deployment and contraction of the distal protection device is accomplished through a mechanical push/pull arrangement.

FIGS. 13A and 13B illustrate a distal protection device 122. FIG. 13A shows device 122 in an undeployed position and FIG. 13B shows device 122 in a deployed position. Distal protection device 122 includes a slotted Nitinol tube 124 which has a lumen 126 extending therethrough. Tube 124 has a plurality of slots 128 at a distal region thereof. The distal portion of slots 128 are covered by mesh 130 which, in the preferred embodiment, is a flexible microporous membrane. Device 122 also preferably includes a mandrel 132 which extends through the inner lumen 126 of tube 124 and is attached to the distal end of tube 124. In the preferred embodiment, mandrel 132 is attached to the distal end of tube 124 by an appropriate adhesive, brazing, welding, or another suitable connection technique. Tube 124 also has, on its inner periphery in a proximal region thereof, a plurality of locking protrusions 134. Lock protrusions 134 are preferably arranged about a proximal expandable region 136 disposed on mandrel 132.

In order to deploy device 122 into the deployed position shown in FIG. 13B, the operator preferably first advances tube 124 distally of the lesion to be fragmented. In the preferred embodiment, tube 124 has a size on the order of a guidewire, such as a 0.014 inch outer diameter. Therefore, it easily advances beyond the stenosis to be fragmented. The operator then pushes on the proximal region of tube 124 and pulls on the proximal end of mandrel 132. This causes two things to happen. First, this causes the struts formed by slots 128 to expand radially outwardly, and carry with them, microporous membrane 130. Thus, microporous membrane 130 forms a generally basket-shaped filter assembly which opens toward the proximal end of tube 124. In addition, proximal expandable member 136 expands and engages protrusions 134. This locks device 122 in the deployed and expanded position. In order to move the device 122 to the collapsed position, the physician simply pushes on mandrel 132 and pulls on the proximal end of tube 124. This causes device 122 to return to the undeployed position shown in FIG. 13A.

It should be noted that device 122 can optionally be provided with a stainless steel proximal hypotube attachment. Also, the struts defined by slots 128 can be expanded and retracted using a fluid coupling instead of a mandrel. In other words, the proximal end of tube 124 can be coupled to a pressurizable fluid source. By making slots 128 very thin, and pressurizing the fluid, the struts expand outwardly. Further, by pulling vacuum on the pressurizable fluid, the struts collapse.

FIG. 14A illustrates distal protection device 140 which is similar to that shown in FIGS. 13A and 13B, except that the struts 142 are formed of a metal or polymer material and are completely covered by mesh 144. Mesh 144 includes two mesh portions, 146 and 148. Mesh portion 146 is proximal of mesh portion 148 on device 140 and is a relatively loose mesh which will allow stenosis fragments to pass therethrough. By contrast, mesh 148 is a fairly tight mesh, or a microporous membrane, (or simply loose mesh portion 146 with a microporous membrane or other suitable filter material bonded or cast or otherwise disposed thereover) which does not allow the fragments to pass therethrough and therefore captures and retains the fragments therein. The mesh portions can provide a memory set which, in the relaxed position, is either deployed or collapsed.

FIG. 14B illustrates a device 150 which is similar to device 140 shown in FIG. 14A, except struts 142 are eliminated and the two mesh portions 146' and 148' are simply joined together at a region 152. Also, the two mesh portions 146' and 148' are not two different discrete mesh portions but are formed of the same braided mesh material wherein the braid simply has a different pitch. The wider pitch in region 146' provides a looser mesh, whereas the narrower pitch in region 148' provides a tighter mesh that traps the embolic material.

FIG. 14C illustrates a distal protection device 160 which is similar to that shown in FIG. 14A. However, rather than simply providing a slotted tube, distal protection device 160 includes a plurality of struts 162 on a proximal region thereof and a plurality of struts 164 on the distal region thereof. Struts 162 are spaced further apart than struts 164 about the periphery of protection device 160. Therefore, struts 162 define openings 166 which are larger than the openings 168 defined by struts 164 and allow stenosis fragments to pass therethrough. Also, struts 164 have secured to the interior surface thereof a filter or mesh portion 170. When deployed, filter portion 170 forms a substantially basket-shaped filter device opening toward the proximal region of tube 172.

FIG. 15 illustrates the operation of another distal protection device 176. Distal protection device 176 includes a tube 178 and a push/pull wire 180. Tube 178 has, at the distal end thereof, a filter assembly 182. Filter assembly 182 includes a plurality of preferably metal struts 184 which have a microporous membrane, or other suitable mesh 186 disposed thereon. Tube 178 also preferably includes end cap 188 and umbrella-like expansion structure 190 disposed at a distal region thereof. Expansion structure 190 is connected to the distal region of tube 178 and to metal struts 184 such that, when push/pull wire 180 is pulled relative to tube 178, expansion member 190 exerts a radial, outwardly directed force on struts 184 causing them to expand radially outwardly relative to the outer surface of tube 178. This causes microporous membrane or mesh 186 to be deployed in a manner opening toward the proximal end of tube 178 to catch embolic material. Struts 184 can also be formed of an appropriate polymer material.

FIGS. 16A and 16B illustrate a protection device in accordance with another embodiment of the present invention. FIG. 16A illustrates distal protection device 192. Device 192 includes guidewire 194, actuator wire 196, and filter assembly 198. Filter assembly 198 includes an expandable ring 200, such as an expandable polymer or metal or other elastic material, which has attached thereto mesh 202. Mesh 202 is also attached to guidewire 194 distally of ring 200. Actuator wire 196 is attached to sleeve or sheath 204 which is positioned to fit about the outer periphery of expandable ring 200, when expandable ring 200 is in the collapsed position.

Thus, when sheath 204 is moved distally of expandable ring 200, expandable ring 200 has shape memory which causes it to expand into the position shown in FIG. 16A. Alternatively, when sheath 204 is pulled proximally by pulling actuator wire 196 relative to guidewire 194, sheath 204 collapses ring 200 and holds ring 200 in the collapsed position within sheath 204. Manipulating wires 194 and 196 relative to one another causes device 192 to move from the deployed position to the collapsed position, and vice versa.

FIG. 16B is similar to device 192 except that, instead of having an expandable ring 200 connected at one point to wire 194, distal protection device 206 includes expandable member 208 which is formed of an elastic coil section of wire 194. Thus, elastic coil section 208 has a shape memory which causes it to expand into the generally helical, conical shape shown in FIG. 16B. However, when sheath 204 is pulled proximally relative to expandable member 208, this causes sheath 204 to capture and retain expandable member 208 in a collapsed position. When sheath 204 is again moved distally of expandable member 208, expandable member 208 returns to its expanded position shown in FIG. 16B carrying with it mesh 210 into a deployed position. In the preferred embodiment, sheath 204 is formed of a suitable polymer material and expandable member 208 and expandable ring 200 are preferably formed of Nitinol.

FIGS. 17A and 17B illustrate the operation of another distal protection device 212. Protection device 212 includes guidewire 214 and filter assembly 216. In the preferred embodiment, filter assembly 216 includes a wire braid portion 218 which extends from a distal region of guidewire 214 proximally thereof. Braid portion 218 is formed of braided filaments or fibers which have a shape memory causing them to form a deployed, basket-shaped filter, such as that shown in FIG. 17A, in the unbiased position. Braided portion 218 terminates at its proximal end in a plurality of eyelets 220. One or more cinch wires 222 are preferably threaded through eyelets 220. By pushing on guidewire 214 and pulling on cinch wires 222, the operator is able to cinch closed, and pull proximally, the proximal portion of mesh 218. This causes mesh 218 to collapse tightly about the outer surface of wire 214.

Therefore, during operation, the operator holds mesh 218 in the collapsed position and inserts protection device 212 distally of the desired stenosis. The operator then allows cinch wire 222 to move distally relative to guidewire 214. This allows mesh 218 to open to the deployed position shown in FIG. 17A which has an outer diameter that approximates the inner diameter of the lumen within which it is disposed. Filter assembly 216 is then disposed to capture embolic material from blood flowing therethrough. Once the embolic material is captured, the operator again moves cinch wire 222 proximally relative to guidewire 214 to collapse filter assembly 216 and capture and retain the embolic material in filter assembly 216. The device 212 is then removed.

FIG. 17B shows distal protection device 212 except that in the embodiment shown in FIG. 17B, protection device 212 is not disposed distally of the stenosis, but rather proximally. This results, for example, in an application where the blood flow is proximal of the stenosis rather than distal. Further, in the embodiment shown in FIG. 17B, guidewire 214 is preferably hollow and the cinch wire 222 extends through the lumen therein. By pushing on guidewire 214, a force is exerted on mesh 218 in the distal direction. This causes cinch wire 222 to tightly close the distal opening in filter assembly 216 and to collapse mesh portion 218. By contrast, by allowing cinch wire 222 to move distal relative to hollow guidewire 214, mesh portion 218 expands and filter assembly 216 is deployed as shown in FIG. 17B.

FIGS. 18A and 18B illustrate a distal protection device 250 in accordance with another aspect of the present invention. Device 250 includes inner wire 252 and outer tube 254. In the preferred embodiment, inner wire 252 is a core wire and outer tube 254 has a lumen 256 therein large enough to accommodate longitudinal movement of inner wire 252 therein. Also, in the preferred embodiment, inner wire 252 has, coupled to its distal end 258, a spring tip 260.

Device 250 includes expandable mesh or braid portion 262. Expandable portion 262 has a proximal end 264 which is attached to the distal end 266 of tube 254. Also, expandable member 262 has a distal end 268 which is attached to the distal end 258 of inner wire 252.

Expandable member 262 is preferably a mesh or braided material which is coated with polyurethane. In one preferred embodiment, a distal portion of expandable member 262 has a tighter mesh than a proximal portion thereof, or has a microporous membrane or other suitable filtering mechanism disposed thereover. In another preferred embodiment, expandable member 262 is simply formed of a tighter mesh or braided material which, itself, forms the filter. FIG. 18A illustrates device 250 in a collapsed, or insertion position wherein the outer diameter of mesh portion 262 closely approximates the outer diameters of either inner wire 252 or outer tube 254.

FIG. 18B illustrates device 250 in the deployed position in which expandable member 262 is radially expanded relative to the collapsed position shown in FIG. 18A. In order to deploy device 250, the outer tube 254 is moved distally with respect to inner wire 252 such that the distal ends 266 and 258 of wires 254 and 252 move longitudinally toward one another. Relative movement of ends 266 and 258 toward one another causes the mesh of expandable member 262 to buckle and fold radially outwardly. Thus, the outer diameter of expandable member 262 in the deployed position shown in FIG. 18B closely approximates the inner diameter of a vessel within which it is deployed.

FIG. 18C illustrates device 250 in a partially collapsed position. In FIG. 18C, the distal end 266 of outer tube 254 and the distal end 258 of inner wire 252 are moved even closer together than they are as shown in FIG. 18B. This causes expandable mesh portion 262 to fold over itself and form a rolling, proximally directed flap 270. As longitudinal movement of inner wire 252 proximally with respect to outer tube 254 continues, mesh portion 262 continues to fold over itself such that the rolling flap portion 270 has an outer radial diameter which continues to decrease. In other words, expandable mesh portion 262 continues to fold over itself and to collapse over the outer periphery of outer tube 254.

FIG. 18D illustrates device 250 in a fully collapsed position in which it retains emboli captured therein. In FIG. 18D, the distal end 266 of outer tube 254 has been advanced as far distally as it can relative to the distal end 258 of inner wire 252. This causes expandable mesh portion 262 to fold all the way over on itself such that it lies against, and closely approximates the outer diameter of, outer tube 254. Device 250 thus captures any emboli filtered from the vessel within which it was deployed, and can be removed while retaining that embolic material.

FIG. 19 illustrates device 280 which depicts a further aspect in accordance with the present invention. Device 280 includes outer tube 282, core wire 284, transition tube 286, movable plunger 288, expandable member 290, fixed collar 292 and bias member 294.

In the preferred embodiment, tube 282 comprises a proximal hypotube which is coupled to a plunger that selectively provides fluid under pressure through an inflation lumen 296. Inner wire 284 is preferably a tapered core wire which terminates at its distal end in a spring coil tip 298 and which is coupled at its proximal end 300 to transition tube 286. Transition tube 286 is preferably an outer polymer sleeve either over hypotube 282, or simply disposed by itself and coupled to a hypotube 282. Transition tube 286 is capable of withstanding the inflation pressure provided by the fluid delivered through the inflation lumen 296.

Movable collar 288 is preferably slidably engageable with the interior surface of transition tube 286 and with the exterior surface of core wire 284, and is longitudinally movable relative thereto. Slidable collar 288 has, attached at its distal end, bias spring 294 which is preferably coiled about core wire 284 and extends to fixed collar 292. Fixed collar 292 is preferably fixedly attached to the exterior surface of a distal portion of core wire 284.

Expandable member 290 is preferably formed, at a proximal portion thereof, of either discrete struts, or another suitable frame (such as a loose mesh) which allows blood and embolic material to flow therethrough. The proximal end 302 of expandable member 290 is coupled to a distal region of movable collar 288. The distal portion of expandable member 290 is preferably formed of a filtering material which is suitable for allowing blood flow therethrough, but which will capture embolic material being carried by the blood.

In one preferred embodiment, spring 294 is biased to force collars 288 and 292 away from one another. Thus, as spring 294 urges collars 288 and 292 away from one another, collar 288 retracts within transition tube 286 pulling expandable member 290 into a collapsed position about core wire 284. However, in order to deploy collapsible member 290 as shown in FIG. 19, the operator preferably actuates a plunger (not shown) which delivers pressurized fluid through lumen 296. The pressurized fluid enters transition tube 286 and travels about the outer periphery of inner core wire 284, thus forcing movable collar 288 to move distally along core wire 284. This overcomes the spring force exerted by spring 294 thus causing collars 288 and 292 to move toward one another, relatively. This motion causes expandable member 290 to buckle and expand outwardly to the deployed position shown in FIG. 19.

Expandable member 290 is collapsed by releasing the pressure applied through lumen 296 (i.e., by causing the plunger to move proximally). This allows spring 294 to again urge collars 288 and 292 away from one another to collapse expandable member 290. In an alternative embodiment, the frame supporting expandable member 290 is imparted with a memory (such as a heat set, or a thermally responsive material which assumes a memory upon reaching a transition temperature) such that the resting state of the frame supporting expandable member 290 is in a collapsed position. This eliminates the need for spring 294. The expandable member 290, in that preferred embodiment, is expanded using the hydraulic pressure provided by the pressurized fluid introduced through lumen 296, and it is collapsed by simply allowing the memory in expandable member 290 to force fluid from transition tube 286 back through lumen 296.

FIGS. 20A and 20B illustrate another aspect in accordance with the present invention. A device 310 includes a mesh portion 312 supported by a frame 314. Expansion of frame 314 to the radially expanded position shown in FIG. 20A is driven by an expandable member, such as a balloon, 316 which is coupled to frame 314. Balloon 316 is coupled to a distal end of a distal hypotube 318, which is formed of a suitable material, such as nitinol. It should be noted that the distal tip of hypotube 318 includes a spring tip 320.

Distal hypotube 318 is shown coupled to a proximal hypotube 322 which has a tapered portion 324 therein. In the preferred embodiment, proximal hypotube 322 is formed of a suitable material, such as stainless steel. A plunger 326 is longitudinally movable within the lumen of both proximal hypotube 322 and distal hypotube 318.

Frame 314, and consequently mesh portion 312, are deployed by the operator moving plunger 326 distally within the lumens of hypotubes 318 and 322. This causes pressurized fluid to enter balloon 316, thereby inflating balloon 316 and driving deployment of frame 314 and mesh 312. In order to collapse frame 314 and mesh 312, the operator preferably moves plunger 326 proximally within the lumens of tubes 318 and 322 to withdraw fluid from within balloon 316. Alternatively, mesh 312 or frame 314 can have a memory set which is either in the inflated or collapsed position such that the operator need only affirmatively move frame 314 and mesh 312 to either the deployed or collapsed position, whichever is opposite of the memory set.

In either case, it is desirable that the operator be able to lock plunger 326 in a single longitudinal position relative to hypotubes 318 and 322. Thus, device 310 includes a locking region 328.

FIG. 20B illustrates locking region 328 in greater detail. FIG. 20B illustrates that, in locking region 328, plunger 326 has a plurality of grooves 330 formed in the outer radial surface thereof. Also, in accordance with the present invention, FIG. 20B illustrates that one of hypotubes 318 or 322 has an inwardly projecting portion 332. In one preferred embodiment, inwardly projecting portion 332 includes an inwardly extending, deflectable, annular rim which extends inwardly from either hypotube 318 or 322. In another preferred embodiment, the inwardly projecting portion 332 includes a plurality of discrete fingers which extend inwardly from one of hypotubes 318 or 322 and which are angularly displaced about the interior periphery of the corresponding hypotube 318 or 322.

In operation, as the operator advances plunger 326 distally within the lumens of hypotubes 318 and 322, inwardly projecting portion 332 rides along the exterior periphery of plunger 326 until it encounters one of grooves 330. Then, inwardly projecting portion 332 snaps into the groove 330 to lock plunger 326 longitudinally relative to tubes 318 and 322.

It should be noted that, in the preferred embodiment, both inwardly projecting portions 332 and grooves 330 are formed such that, when gentle pressure is exerted by the operator on plunger 326 relative to hypotubes 318 and 322, projection portions 332 follow the contour of grooves 330 up and out of grooves 330 so that plunger 326 can again be freely moved within the lumens of hypotubes 318 and 322. Thus, the relative interaction between projecting portions 332 and grooves 330 provides a ratcheting type of operation wherein plunger 326 can be releasably locked into one of a plurality longitudinal positions relative hypotubes 318 and 322, since a plurality of grooves 330 are provided. Plunger 326 can be moved back and forth longitudinally within the lumens of hypotubes 318 and 322 in a ratcheting manner and can be locked into one of a plurality of relative longitudinal positions because there are a plurality of grooves 330 in the exterior of plunger 326. It should also be noted, however, that in another preferred embodiment, a plurality of sets of inwardly projecting portions 332 are provided along the inner longitudinal surface of hypotubes 318 and/or 322. In that case, only a single groove 330 needs to be formed in the exterior surface of plunger 326, and the same type of ratcheting locking operation is obtained.

In the preferred embodiment, at least the exterior of hypotubes 318 and 322, and preferably the exterior of plunger 326, are tapered. This allows device 310 to maintain increased flexibility. It should also be noted that, in the preferred embodiment, hypotubes 318 and 322 are preferably sized as conventional guidewires.

Therefore, it can be seen that the present invention provides a filter assembly which can either be biased in the deployed position in which it is expanded radially away from the shaft used to deploy it, or it can be biased in a collapsed position in which it lies against that shaft and closely approximates the outer diameter of that shaft. In either case (and in one embodiment of the present invention), forcing movement of fluid either into or out of the expandable member drives the filter to move between the contracted and expanded positions, or vice versa. In another embodiment, using a push/pull mechanical manipulation causes the filter to move between the contracted and expanded positions. By providing such an expandable filter on a guidewire-sized shaft, the present invention provides a number of advantages. First, the present invention can be used with many forms of dilatation devices while facilitating such use over the guidewire used in actuating the filter. Further, the present invention can be utilized without prior art methods of capturing fragments of stenosis, and without the associated problems.

Further, in the present invention, the preferred guidewire used to deploy the filter has an approximate inside diameter of 0.014 inches and an outside diameter of approximately 0.018 inches. For other coronary applications, different dimensions may also be used, such as outer diameters of approximately 0.010 inches or 0.014 inches. Further, it will be appreciated that the particular size of the guidewire will vary with application. Applications involving neural vasculature will require the use of a smaller guidewire, while other applications will require the use of a larger guidewire.

It should be noted that all of the devices according to the present invention can optionally be coated with an anti-thrombotic material, such as heparin, to inhibit clotting.

Although the present invention has been described with reference to preferred embodiments, workers skilled in the art will recognize that changes may be made in form and detail without departing from the spirit and scope of the invention.

What is claimed is:

1. An emboli capturing system for introduction into vasculature to capture emboli in blood flowing in the vasculature, the emboli capturing system comprising:

a guidewire;

an emboli capturing device operably coupled to a distal portion of the guidewire, the emboli capturing device having a first end coupled to the guidewire and a second, expandable end; and a cinch assembly disposed at the second end of the emboli capturing device, the cinch assembly including a cinching actuator extending proximally, actuation of the cinch actuator retracting the second end of the emboli capturing device.

2. The emboli capturing system of claim 1 wherein the emboli capturing device comprises a mesh.

3. The emboli capturing system of claim 1 wherein the guidewire has a lumen extending therethrough and wherein the cinch actuator extends from the second end of the emboli capturing device, proximally through the lumen.

4. The emboli capturing system of claim 1 wherein the second end of the emboli capturing device opens distally.

5. The emboli capturing system of claim 1 wherein the second end of the emboli capturing device opens proximally.

6. The emboli capturing system of claim 1 wherein the guidewire has a lumen extending at least through a distal region thereof and wherein the first end of the emboli capturing device is disposed within the lumen.

7. The emboli capturing system of claim 1 wherein the cinch assembly includes a plurality of eyelets disposed at the second end of the emboli capturing device and wherein the cinching actuator includes a wire, threaded through the eyelets.

8. The emboli capturing system of claim 1 wherein the emboli capturing device, when in a collapsed position, has an outer diameter approximating an outer diameter of the guidewire.

9. The emboli capturing system of claim 1 wherein the emboli capturing device is biased in a collapsed position in which it has an outer diameter approximating the outer diameter of the guidewire, and wherein the emboli capturing device includes an expansion actuator actuable to expand and deploy the emboli capturing device radially outwardly relative to the guidewire.

10. The emboli capturing system of claim 1 wherein the emboli capturing device is biased in a deployed position in which it is expanded radially outwardly relative to the guidewire, and wherein actuation of the cinching actuator causes the emboli capturing device to move to a retracted position wherein the emboli capturing device has an outer diameter approximating an outer diameter of the guidewire.

* * * * *